United States Patent [19]

George et al.

[11] Patent Number: 4,945,096

[45] Date of Patent: Jul. 31, 1990

[54] TREATMENT OF A DEPRESSIVE STATE WITH 2-[(4-PIPERIDYL)METHYL]-1,2,3,4-TETRAHYDROISOQUINOLINE DERIVATES

[75] Inventors: Pascal George, Vitry-sur-Seine; Mireille Sevrin, Paris, both of France

[73] Assignee: Synthelabo, Paris, France

[21] Appl. No.: 400,811

[22] Filed: Aug. 30, 1989

Related U.S. Application Data

[62] Division of Ser. No. 228,748, Aug. 5, 1988, Pat. No. 4,885,302.

[30] Foreign Application Priority Data

Aug. 7, 1987 [FR] France .................. 87 11288
Dec. 30, 1987 [FR] France .................. 87 18342
Apr. 19, 1988 [FR] France .................. 88 05129
Apr. 19, 1988 [FR] France .................. 88 05130

[51] Int. Cl.$^5$ .............................................. A61K 31/47
[52] U.S. Cl. ..................................... 514/307; 546/145; 546/146; 546/148; 546/150
[58] Field of Search ............................................ 514/307

[56] References Cited

U.S. PATENT DOCUMENTS

| | | | |
|---|---|---|---|
| 2,922,786 | 1/1960 | DeWitt | 546/150 |
| 3,634,410 | 1/1972 | Tvaermose et al. | 260/293.64 |
| 4,261,998 | 4/1981 | Najer | 546/146 |
| 4,495,354 | 1/1985 | Coffen | 546/150 |

OTHER PUBLICATIONS

Campbell, et al., "Chemical Abstracts", vol. 92, 1980, col. 92:181222s.
George, et al., "Chemical Abstracts", vol. 110, 1989, col. 110:231451d.
George, et al., "Chemical Abstracts", vol. 111, 1989, col. 174006g.

Primary Examiner—Glennon H. Hollrah
Assistant Examiner—James H. Turnipseed
Attorney, Agent, or Firm—Fleit, Jacobson, Cohn, Price, Holman & Stern

[57] ABSTRACT

A compound of formula (I)

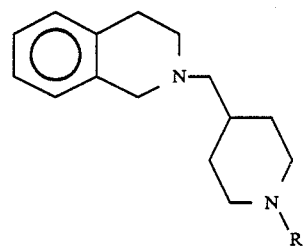

in which R is (a) a hydrogen atom;
(b) a linear or branched ($C_1$–$C_6$) alkyl group; an allyl group; a cycloalkylmethyl group in which the cycloalkyl moiety has from 3 to 6 carbon atoms; a phenylmethyl group unsubstituted or substituted with one to three substituents chosen from halogen atoms and trifluoromethyl, nitro, amino, dimethylamino, cyano, aminocarbonyl, linear or branched ($C_1$–$C_3$) alkyl, liner or branched ($C_1$–$C_3$) alkoxy and linear or branched ($C_1$–$C_3$) alkylthio groups; a 2-phenylethyl group; a 3-phenylpropyl group; a 3-phenyl-2-propenyl group; a phenylcarbonylmethyl group; a naphthylmethyl group; a pyridylmethyl group; a furylmethyl group; or a thienylmethyl group; or
(c) a linear or branched ($C_2$–$C_6$) alkanoyl group; a cycloalkylcarbonyl group in which the cycloalkyl moiety has from 3 to 6 carbon atoms; a trifluoroacetyl group; a phenylcarbonyl group unsubstituted or substituted with one to three substituents chosen from halogen atoms and trifluoromethyl, nitro, linear or branched ($C_1$–$C_3$) alkyl, linear or branched ($C_1$–$C_3$) alkoxy and linear or branched ($C_1$–$C_3$) alkylthio groups; a 1-oxo-3-phenyl-2-propenyl group; a naphthylcarbonyl group; a pyridylcarbonyl group; a furylcarbonyl group; a thienylcarbonyl group; a (2-indolyl)carbonyl group; or a (5-indolyl)carbonyl group; or a pharmacologically acceptable acid addition salt thereof.

1 Claim, No Drawings

TREATMENT OF A DEPRESSIVE STATE WITH 2-[(4-PIPERIDYL)METHYL]-1,2,3,4-TETRAHYDROISOQUINOLINE DERIVATES

This application is a divisional of application Ser. No. 228,748, filed Aug. 5, 1988, now U.S. Pat. No. 4,885,302, issued Dec. 5, 1989.

The present invention relates to 2-[(4-piperidyl)methyl]-1,2,3,4-tetrahydroisoquinoline derivatives, to their preparation and to pharmaceutical compositions containing them.

The present invention provides a compound of formula (I) as shown in scheme 1 on the following page, in which R is, (a) a hydrogen atom;
(b) a linear or branched ($C_1$–$C_6$) alkyl group, for example a methyl group; an allyl group; a cycloalkylmethyl group in which the cycloalkyl moiety has from 3 to 6 carbon atoms, for example a cyclohexyl moiety; a phenylmethyl group unsubstituted or substituted with one to three substituents chosen from halogen atoms, for example chlorine or fluorine atoms, and trifluoromethyl, nitro, amino, dimethylamino, cyano, aminocarbonyl, linear or branched ($C_1$–$C_3$) alkyl, linear or branched ($C_1$–$C_3$) alkoxy, for example methoxy or ethoxy, and linear or branched ($C_1$–$C_3$) alkylthio, for example methylthio, groups; a 2-phenylethyl group; a 3-phenylpropyl group; a 3-phenyl-2-propenyl group; a phenylcarbonylmethyl group; a naphthylmethyl group; a pyridylmethyl group; a furylmethyl group; a thienylmethyl group; or
(c) a linear or branched ($C_2$–$C_6$) alkanoyl group, for example an acetyl group; a cycloalkylcarbonyl group in which the cycloalkyl moiety has from 3 to 6 carbon atoms, for example

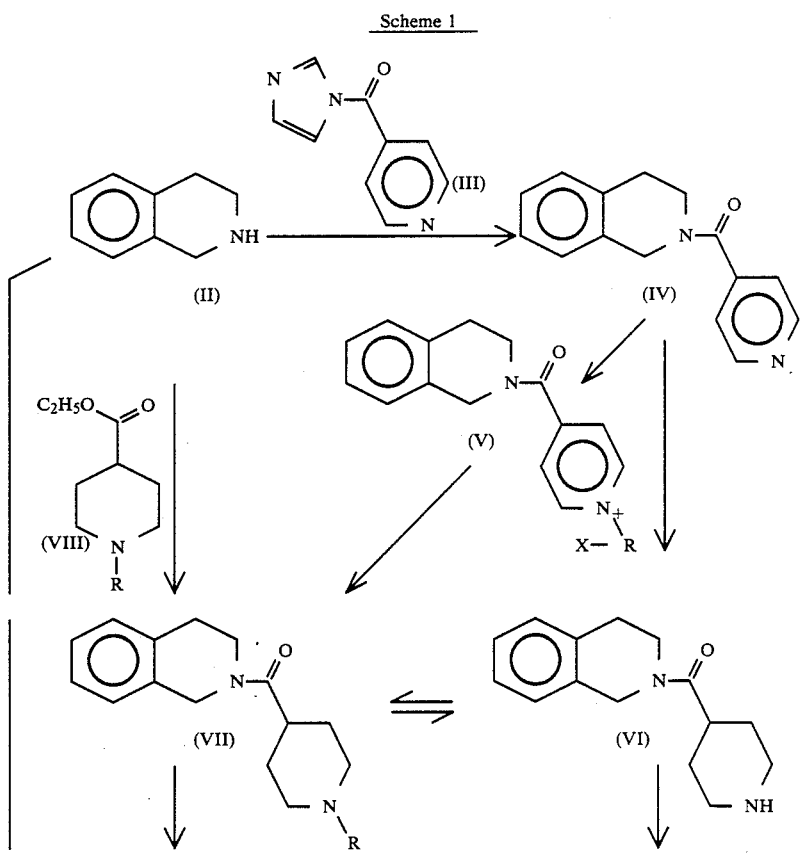

Scheme 1

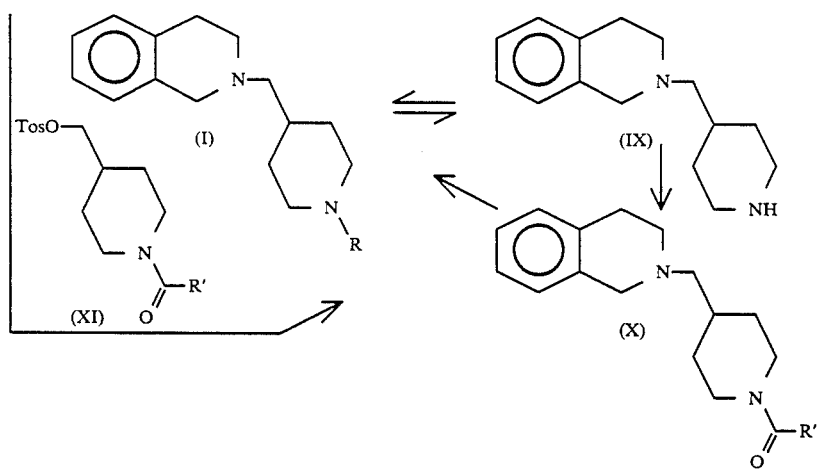

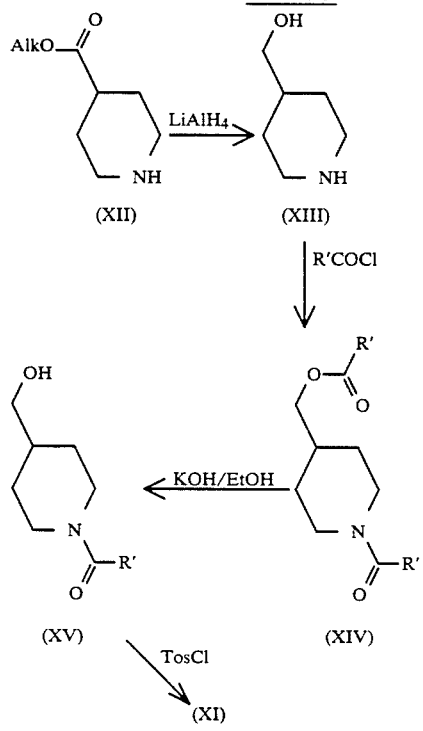

a cyclohexyl moity; a trifluoroacetyl group; a phenylcarbonyl group unsubstituted or substituted with one to three substituents chosen from halogen atoms, for example chlorine or fluorine atoms, and trifluoromethyl, nitro, linear or branched ($C_1$-$C_3$) alkyl, for example methyl, linear or branched ($C_1$-$C_3$) alkoxy, for example methoxy or ethoxy, and linear or branched ($C_1$-$C_3$) alkylthio, for example methylthio, groups; a 1-oxo-3-phenyl-2-propenyl group; a naphthylcarbonyl group; a pyridylcarbonyl group; a furylcarbonyl group; a thienylcarbonyl group; a (2-indolyl)carbonyl group; or a (5-indolyl) carbonyl group; or a pharmacologically acceptable acid addition salt thereof, for example a fumarate, difumarate, hydrochloride or dihydrochloride salt.

The substituents on the phenyl rings may be in the 2,3 or 4 position if there is one substituent, in the 2, 3; 2, 4; 2, 5; 3, 4 or 3, 5 positions if there are two substituents or in the 2,3,4; 2,3,5; 2,3,6; 2,4,5 or 2, 4, 6 positions if there are three substituents.

Preferred compounds are shown in the following Table. They may be present in the form of the free base or as any other pharmacologically acceptable acid addition salt apart from the ones shown.

TABLE (I)

| No | R | Salt | M.p. (°C.) |
|---|---|---|---|
| 1 | H | diHCl | 252–255 |
| 2 | $CH_3$ | difum. | 157–158 |
| 3 | $C_6H_5$—$CH_2$— | diHCl | 259–264 |
| 4 | 2-Cl—$C_6H_4$—$CH_2$— | difum. | 209–211 |
| 5 | 3-Cl—$C_6H_4$—$CH_2$— | difum. | 188–190 |
| 6 | 4-Cl—$C_6H_4$—$CH_2$— | difum. | 205–207 |
| 7 | 2-$CH_3$—$C_6H_4$—$CH_2$— | difum. | 182–183 |
| 8 | 3-$CH_3$—$C_6H_4$—$CH_2$— | difum. | 185–186 |
| 9 | 4-$CH_3$—$C_6H_4$—$CH_2$— | difum. | 190.5–193 |
| 10 | 2-$CH_3O$—$C_6H_4$—$CH_2$— | difum. | 177–180 |
| 11 | 3-$CH_3O$—$C_6H_4$—$CH_2$— | difum. | 173–174 |
| 12 | 4-$CH_3O$—$C_6H_4$—$CH_2$— | difum. | 204–206.5 |
| 13 | $C_6H_5$—$CH_2$—$CH_2$— | difum. | 212–213 |
| 14 | $C_6H_4$—CO— | HCl | 228–235 |
| 15 | 2-Cl—$C_6H_4$—CO— | fum. | 95–98 |
| 16 | 3-Cl—$C_6H_4$—CO— | HCl | 162–163 |
| 17 | 4-Cl—$C_6H_4$—CO— | fum. | 168–170 |
| 18 | 2-$CH_3$—$C_6H_4$—CO— | fum.(1) | 115–120 |
| 19 | 3-$CH_3$—$C_6H_4$—CO— | fum. | 149–151 |
| 20 | 4-$CH_3$—$C_6H_4$—CO— | fum. | 134–136 |
| 21 | 2-$OCH_3$—$C_6H_4$—CO— | fum. | 110–111 |
| 22 | 3-$OCH_3$—$C_6H_4$—CO— | fum. | 127–128 |
| 23 | 4-$OCH_3$—$C_6H_4$—CO— | fum. | 132–133 |
| 24 | 2-F—$C_6H_4$—CO— | fum. | 131–133 |
| 25 | 3-F—$C_6H_4$—CO— | fum. | 166–167 |
| 26 | 4-F—$C_6H_4$—CO— | fum. | 172–174 |
| 27 | 3-$CF_3$—$C_6H_4$—CO— | fum. | 162 ± 164 |
| 28 | 4-$CF_3$—$C_6H_4$—CO— | fum. | 194–195 |
| 29 | 4-$NO_2$—$C_6H_4$—CO— | HCl | 209–210 |
| 30 | 4-$SCH_3$—$C_6H_4$—CO— | fum. | 164–166 |
| 31 | 3,5-$Cl_2$—$C_6H_3$—CO— | fum. | 165–166 |
| 32 | 2,3-$(OCH_3)_2$—$C_6H_3$—CO— | fum. | 185–186 |
| 33 | 3,5-$(OCH_3)_2$—$C_6H_3$—CO— | fum.(2) | 83–86 |

TABLE-continued (I) Structure: 1,2,3,4-tetrahydroisoquinoline-N-CH2-(4-piperidinyl)-N-R

| No | R | Salt | M.p. (°C.) |
|---|---|---|---|
| 34 | 3,5-(CH$_3$)$_2$—C$_6$H$_3$—CO— | fum. | 90–95 |
| 35 | 3,5-(CF$_3$)$_2$—C$_6$H$_3$—CO— | fum.(3) | 105–108 |
| 36 | C$_{10}$H$_7$-α-CO—* | fum. | 103–107 |
| 37 | C$_{10}$H$_7$-β-CO—* | fum. | 163–165 |
| 38 | CH$_3$—CH$_2$—CH$_2$— | difum. | 186–187 |
| 39 | CH$_2$=CH—CH$_2$— | difum. | >250 |
| 40 | C$_6$H$_5$—CO—CH$_2$— | difum. | 203–205 |
| 41 | C$_6$H$_5$—CH$_2$—CH$_2$—CH$_2$— | difum. | 153–154 |
| 42 | 2-F—C$_6$H$_4$—CH$_2$— | difum. | 189–191 |
| 43 | 3-F—C$_6$H$_4$—CH$_2$— | difum. | 184–186 |
| 44 | 4-F—C$_6$H$_4$—CH$_2$— | difum. | 183–185 |
| 45 | 3,5—F$_2$—C$_6$H$_3$—CH$_2$— | difum. | 188–190 |
| 46 | 3,5-Cl$_2$—C$_6$H$_3$—CH$_2$— | difum. | 198–199 |
| 47 | 3,5-(CH$_3$)$_2$—C$_6$H$_3$—CH$_2$— | difum. | 203–205 |
| 48 | 3,4-(CH$_3$O)$_2$—C$_6$H$_3$—CH$_2$— | difum. | 175–176 |
| 49 | 3,5-(CH$_3$O)$_2$—C$_6$H$_3$—CH$_2$— | difum. | 199–201 |
| 50 | 3-NC—C$_6$H$_4$—CH$_2$— | difum. | 179–181 |
| 51 | 3-H$_2$NCO—C$_6$H$_4$—CH$_2$— | difum. | 182–184 |
| 52 | 3-O$_2$N—C$_6$H$_4$—CH$_2$— | difum. | 216–217 |
| 53 | 3-H$_2$N—C$_6$H$_4$—CH$_2$— | difum. | 163–166 |
| 54 | 3-(CH$_3$)$_2$N—C$_6$H$_4$—CH$_2$— | difum. | 180–182 |
| 55 | 4-CH$_3$S—C$_6$H$_4$—CH$_2$— | difum. | 196–198 |
| 56 | 3-CF$_3$—C$_6$H$_4$—CH$_2$— | difum. | 193–195 |
| 57 | 3,5-(CF$_3$)$_2$—C$_6$H$_3$—CH$_2$— | difum. | 222–224 |
| 58 | 3-C$_2$H$_5$O—C$_6$H$_4$—CH$_2$— | difum. | 190–192 |
| 59 | C$_6$H$_5$—CH=CH—CH$_2$—(trans) | diHCl | 197–198 |
| 60 | 2-pyridyl-CO— | fum. | 115–118 |
| 61 | 3-pyridyl-CO— | fum. | 180–182 |
| 62 | 4-pyridyl-CO— | fum. | 179–180 |
| 63 | 2-thienyl-CO— | fum. | 169–172 |
| 64 | 3-thienyl-CO— | fum. | 174–177 |
| 65 | 2-furyl-CO— | fum. | 151–152 |
| 66 | 3-furyl-CO— | fum. | 171–174 |
| 67 | indol-2-yl-CO— | fum. | 203–206 |
| 68 | indol-5-yl-CO— | fum.(2) | 110–125 |
| 69 | CH$_3$—CO— | fum. | 139–141 |
| 70 | nC$_3$H$_7$—CO— | fum. | 168–170 |
| 71 | cC$_6$H$_{11}$—CO— | fum. | 202–204 |
| 72 | C$_6$H$_5$—CH$_2$—CO— | fum. | 132–136 |
| 73 | CF$_3$—CO— | HCl | 195–196 |
| 74 | C$_6$H$_5$—CH=CH—CO—(trans) | HCl | 214–215 |
| 75 | C$_{10}$H$_7$-α-CH$_2$—* | difum. | 208–212 |
| 76 | C$_{10}$H$_7$-β-CH$_2$—* | difum. | 190–192 |
| 77 | 3-pyridyl-CH$_2$— | difum. | 192–193 |
| 78 | 2-thienyl-CH$_2$— | difum. | 191–193 |
| 79 | 3,4-F$_2$—C$_6$H$_3$—CO— | fum. | 177–179 |
| 80 | 3-C$_2$H$_5$O—C$_6$H$_4$—CO— | fum. | 74–77 |

Notes:
fum.: fumarate
difum.: difumarate
HCl: hydrochloride
diHCl: dihydrochloride
(1)fumarate containing one equivalent of isopropyl alcohol;
(2)fumarate hemihydrate;
(3)fumarate monohydrate;
*C$_{10}$H$_7$-α and C$_{10}$H$_7$-β denote α- and β-naphthyl groups, respectively.

The compounds of formula (I) may be prepared by a process as illustrated in Scheme 1 above.

The present invention provides a process for preparing a compound of formula (I), or a pharmacologically acceptable acid addition salt thereof, in which R is a hydrogen atom, i.e., a compound of formula (IX), or a pharmacologically acceptable acid addition salt thereof, which comprises reducing a compound of formula (VI) as shown in Scheme 1 with lithium aluminium hydride or a simple or complex boron hydride, for example diborane or a borane/methyl sulphide complex, and if desired, forming a pharmacologically acceptable acid addition salt of the compound thus obtained.

The present invention also provides a process for preparing a compund of formula (I), or a pharmacologically acceptable acid addition salt thereof, in which R is a group as defined in (b) above, which comprises reducing a compound of formula (VII) as shown in Scheme 1 in which R is as defined above, with lithium aluminium hydride or a simple or complex boron hydride, for example diborane or a borane/methyl sulphide complex, and if desired, forming a pharmacologically acceptable acid addition salt of the compound thus obtained.

The present invention additionally provides a process for preparing a compound of formula (I), or a pharmacologically acceptable acid addition salt thereof, in which R is a group as defined in (c) above, i.e. a compound of formula (X) as shown in Scheme 1 in which R'CO is a group R as defined above, or a pharmacologically acceptable acid addition salt thereof, which comprises reacting 1,2,3,4-tetrahydroisoquinoline of formula (II) as shown in Scheme 1 with a tosylate of formula (XI) as shown in Scheme 1 in which Tos is a tosylate group and R'CO is as defined above, in the absence or presence of an inert solvent, for example dimethylformamide or xylene, at a temperature of 20° to 150° C., optionally in the presence of an organic or inorganic base, for example a tertiary amine or an alkali metal carbonate or hydrogencarbonate.

The present invention further provides a process for preparing a compound of formula (I), or a pharmacologically acceptable acid addition salt thereof, in which R is a group as defined in (c) above, i.e., a compound of formula (X) in which R'CO is a group R as defined above, or a pharmacologically acceptable acid addition salt thereof, which comprises reacting a compound of formula (I) in which R is hydrogen, i.e., a compound of formula (IX), with a compound of formula RY in which R is as defined above and Y is a labile group, for example a halogen atom such as a chlorine atom, a 1-imidazolyl group, a $C_1$–$C_6$ alkoxy group or an acyloxy group of formula R'CO$_2$ wherein R'CO is the group R as defined above, and if desired, forming a pharmacologically acceptable acid addition salt of the compound thus obtained.

For example when Y is a halogen atom the reaction may be carried out in the presence of an organic base, for example triethylamine, in a solvent, for example dichloromethane or ethyl acetate. When Y is a 1-imidazoyl group the compound of formula RY may be prepared in situ from the corresponding acid of formula ROH and N,N'-carbonyldiimidazole. The reaction may, for example, be carried out in a solvent, such as tetrahydrofuran. When Y is a $C_1$–$C_6$ alkoxy group the compound of formula (IX) may, for example, be reacted with a trialkylaluminium, for example trimethylaluminium, and the complex thus formed reacted with the compound of formula RY, for example at a temperature of from 50° to 110° C. in an inert aromatic solvent such as toluene. When Y is an acyloxy group of formula R'CO$_2$ the reaction may, for example, be carried out in an inert solvent or the compound of formula RY may act as a solvent. A suitable reaction temperature is 0° to 60° C.

The present invention also provides a process for preparing a compound of formula (I), or a pharmacologically acceptable acid addition salt thereof, in which R is a group as defined in (b) above, which comprises reducing a compound of formula (I) in which R is a group as defined in (c) above, i.e. a compound of formula (X) with a simple or complex boron hydride, for example diborane or a borane/methyl sulphide complex, or with lithium aluminium hydride or aluminium hydride, in an ethereal solvent, for example diethyl ether, tetrahydrofuran or dioxane, at a temperature of from 20° to 100° C.

The present invention additionally provides a process for preparing a compound of formula (I), or a pharmacologically acceptable acid addition salt thereof, in which R is a group as defined in (b) above, which comprises alkylating a compound of formula (I) in which R is a hydrogen atom, i.e. a compound of formula (IX), with a compound of formula RX in which R is a group as defined in (b) above and X is a labile group, for example a halide atom, and if desired, forming a pharmacologically acceptable acid addition salt of the compound thus obtained.

The present invention further provides a process for preparing a compound of formula (I), or a pharmacologically acceptable acid addition salt thereof, in which R is a hydrogen atom, i.e. a compound of formula (IX), or a pharmacologically acceptable acid addition salt thereof, which comprises hydrogenolysis of a compound of formula (I) in which R is a phenylmethyl group in the presence of palladium, and if desired, forming a pharmacologically acceptable acid addition salt of the compound thus obtained.

The compound of formula (VII) may, for example, be prepared by alkylating a compound of formula (VI) as shown in Scheme 1 in which R is a group as defined in (b) above with a compound of formula RX in which R is as defined above and X is a labile group, for example a halide atom such as a bromine atom.

The compound of formula (VII) may also, for example, be prepared by the catalytic hydrogenation of a compound of formula (V) as shown in Scheme 1 in which R is a group as defined in (b) and X is a labile group, for example a halide atom such as a bromine atom.

The compound of formula (VII) may additionally, for example, be prepared by reacting 1,2,3,4-tetrahydroisoquinoline of formula (II) with an isonipecotate of formula (VIII) as shown in Scheme 1 in which R is as defined in (b), in the presence of trimethylaluminium.

The compound of formula (V) may, for example, be prepared by the alkylation of an amide of formula (IV) as shown in Scheme 1 with a compound of formula RX in which R is a group as defined in (b) and X is as defined above in relation to the compound of formula (V).

The compound of formula (VI) may be prepared, for example, by hydrogenolysis, in the presence of palladium, of a compound of formula (VII) in which R is a phenylmethyl group. It may also, for example, be prepared by catalytic hydrogenation of a compound of formula (IV), for example under the conditions described in US-A-4,243,666.

The compound of formula (IV) may, for example, be prepared by the reaction of 1,2,3,4-tetrahydroisoquinoline with an imidazolide of formula (III) as shown in Scheme 1, prepared in situ from isonicotinic acid and N,N'-carbonyldiimidazole.

The tosylate of formula (XI) may, for example, be prepared according to the method illustrated in Scheme 2 above.

A 4-piperidinecarboxylate of formula (XII) (in which Alk is a lower alkyl group) is reduced, for example by means of lithium aluminium hydride, to obtain 4-piperidinemethanol of formula (XIII), which is reacted with an acid chloride of formula R'COCl, in which R'CO is a group as defined in (b), in an inert solvent, such as a chlorinated solvent, at a temperature of 20° to 80° C. An ester amide of formula (XIV) is thereby obtained, which is saponified, for example by means of sodium hydroxide or potassium hydroxide, in a lower aliphatic alcohol solvent, preferably ethanol, to obtain an alcohol of formula (XV), which is then reacted with tosyl chloride in a basic medium such as pyridine to form the tosylate of formula (XI).

Depending on the substituents present in the group R, it is self-evident that it is possible to convert, by well-known processes, some compounds of formula (I) to other compounds of formula (I) by acting on the said substituents.

Thus, for example, a compound of formula (I) in which R is a phenylmethyl group bearing an aminocarbonyl group may be obtained from a compound of formula (I) in which R is a phenylmethyl group bearing a cyano group, by reacting the latter with gaseous hydrochloride acid in the presence of formic acid.

A compound of formula (I) in which R is a phenylmethyl group bearing an amino group may be obtained from a compound of formula (I) in which R is a phenylmethyl bearing a nitro group, by reduction of the latter by means of diborane or the diborane/methyl sulphide complex, in an ethereal solvent such as tetrahydrofuran.

A compound of formula (I) in which R is a phenylmethyl group bearing a dimethylamino group may be obtained from a compound of formula (I) in which R is a phenylmethyl group bearing an amino group, by reductive amination of the latter, that is to say by reaction with formaldehyde in the presence of an acid such as sulphuric acid, in an ethereal solvent such as tetrahydrofuran, followed by reduction of the adduct thereby obtained by means of sodium borohydride.

The Examples which follow further illustrate the present invention. The elemental microanalyses and the IR and NMR spectra confirm the structures of the products obtained.

The numbers given in brackets in the titles of the examples correspond to those in the table given later.

EXAMPLE 1

(Compound No. 5)

2-[{1-[(3-Chlorophenyl)methyl]-4-piperidyl}methyl]-1,2,3,4-tetrahydroisoquinoline difumarate (a)

2-[(4-Pyridinyl)carbonyl]-1,2,3,4-tetrahydroisoquinoline 50 g (406 mmol) of isonicotinic acid are dissolved under an argon atmosphere in 1000 ml of tetrahydrofuran and 25 g of N,N'-carbonyldiimidazole are added while stirring, the mixture is stirred for half an hour, a further 25 g of N,N'carbonyldiimidazole are added, the mixture is stirred for a further half hour and 15 g of N,N'-carbonyldiimidazole are added. Stirring is continued for 1 h 30 min, 51.39 g (385.8 mmol) of 1,2,3,4-tetrahydroisoquinoline dissolved in a few milliliters of tetrahydrofuran are introduced slowly into the mixture, which has become clear, and the mixture is stirred overnight at room temperature. The solvent is then evaporated off, the oily residue taken up with approximately 700 ml of dichloromethane, and the solution obtained washed twice with saturated sodium bicarbonate solution and thereafter twice with water and dried over magnesium sulphate. 87.48 g of an orange-coloured oil, which solidifies slowly in the cold, are obtained.

(b)

2-[(4-Piperidyl)carbonyl]-1,2,3,4-tetrahydroisoquinoline.

A catalytic hydrogenation of 35 g (127.3 mmol) of 2-[(4-pyridyl)carbonyl]-1,2,3,4-tetrahydroisoquinoline hydrochloride in 600 ml of methanol is performed in the presence of 1.2 g of platinum oxide, for 17 h, under a hydrogen pressure of 0.38 MPa. The catalyst is then filtered off, the methanol evaporated off, the residue taken up with ether and the insoluble material filtered off. 33.7 g of hydrochloride are obtained, from which the base is liberated by introducing it into a mixture of water and dichloromethane, adding potassium carbonate portionwise to pH > 10. The organic phase is separated off and dried over sodium sulphate and the solvent evaporated off.

The residue is recrystallized in ether, filtered off, washed with pentane and dried. 17.2 g of base are obtained. Melting point: 200°-205° C. (decomposition).

(c)

2[{1-[(3-Chlorophenyl)methyl]-4-piperidyl}carbonyl]-1,2,3,4-tetrahydroisoquinoline 5.2 g (21.3 mmol) of 2-[(4-piperidyl)carbonyl]-1,2,3,4-tetrahydroisoquinoline, 4.94 g (25.5 mmol) of 1-bromo-3-(chloromethyl)benzene and 4.71 g (34 mmol) of potassium carbonate are introduced into 100 ml of anhydrous acetone. The mixture is stirred overnight at room temperature, the acetone then evaporated off, the residue taken up with dichloromethane and water, the organic phase is separated off, washed and dried and the solvent evaporated off. 10.5 g of product are obtained, and this is purified by chromatography on a silica column, first with dichloromethane and then with a 97:3 dichloromethane/methanol mixture. The purified product is taken up with pentane and the latter evaporated off. 6.13 g of pure base are obtained. Melting point: 114°115° C.

(d)

2-[{1-[(3-Chlorophenyl)methyl]-4-piperidiyl}methyl]-1,2,3,4-tetrahydroisoquinoline difumarate 4.5 g (12.2 mmol) of 2-[{1-[(3-chlorophenyl)methyl]-4-piperidyl}carbonyl]-1,2,3,4-tetrahydroisoquinoline are dissolved in 70 ml of tetrahydrofuran, 3.66 ml (36.6 mmol) of a 10N solution of borane/methyl sulphide complex are added, and the mixture is heated to 50° C. for 2 h and stirred for 2 days at room temperature. The mixture is then hydrolysed with 20 ml of methanol followed by 10 ml of concentrated hydrochloric acid, heated under reflux for 3 h and left standing overnight. The solvent is evaporated off and the residue taken up with ether and water, and the aqueous phase is separated off, 30% strength aqueous sodium bicarbonate is added to it to pH > 10 and it is extracted with dichloromethane. The organic phase is separated off, washed with water and dried over sodium sulphate and the solvent evaporated off. 4.5 g of a clear oil are obtained, and this is purified by chromatography on a silica column eluting with a 98:2 dichloromethane/methanol mixture. 3.8 g of oil are obtained; this is dissolved in ethyl acetate and this solution is poured dropwise into a solution of fumaric acid in the minimum amount of methanol. The precipitated salt is filtered off, washed with ethyl acetate, acetone and ether and dried. 3.9 g of difumarate are obtained. Melting point: 188°-190° C. (decomposition).

EXAMPLE 2

(Compound No. 3)

2-[(1-Phenylmethyl-4-piperidyl)methyl]-1,2,3,4-tetrahydroisoquinoline dihydrochloride (a)

2-[(1-Phenylmethyl-4-piperidyl)carbonyl]-1,2,3,4-tetrahydroisoquinoline 251 ml (594 mmol) of trimethylaluminium (at a concentration of 25% in hexane) are introduced under an argon atmosphere into 400 ml of toluene. The solution is cooled in an ice bath and 81.5 g (612 mmol) of 1,2,3,4-tetrahydroisoquinoline, dissolved in 200 ml of toluene, are added. The mixture is heated to approximately 50° C. and 95 g (384 mmol) of ethyl 1-phenylmethyl-4-piperidinecarboxylate, dissolved in 400 ml of toluene, are added. The mixture is heated under reflux for 2 h, approximately 250 ml of solvent being removed by means of a Dean and Stark apparatus. The mixture is cooled in an ice bath and hydrolysed by slowly adding 250 ml of water, and the insoluble material is filtered off, it being rinsed with ethyl acetate. The filtrate is washed three times with water, the organic phase dried over sodium sulphate, the solvent evaporated off and the residue recrystallized in cyclohexane. 116.6 g of product are obtained. Melting point: 98°–100° C.

(b)

2-[(1-Phenylmethyl-4-piperidyl)methyl]-1,2,3,4-tetrahydroisoquinoline dihydrochloride First variant 8 g (24 mmol) of 2-[(1-phenylmethyl-4-piperidyl)carbonyl]-1,2,3,4-tetrahydroisoquinoline are introduced under an argon atmosphere into 150 ml of tetrahydrofuran, 5 g (133 mmol) of sodium borohydride are added, the mixture is cooled to −10° C., 19 ml (155 mmol) of boron trifluoride/ether complex are added and the mixture is stirred for 1 h at −10° C. The mixture is hydrolysed at 0° C. with 66 ml of 1N hydrochloric acid, neutralized with concentrated ammonia solution and extracted with dichloromethane. The organic phase is separated off, washed twice with water and dried, and the solvent evaporated off. The residue is taken up with 200 ml of ethanol, a stream of gaseous hydrochloric acid is passed through it and the mixture is heated under reflux for 6 h. The solvent is evaporated off, the residue taken up with ether and water, concentrated ammonia solution added, the organic phase separated off, washed with water and dried and the solvent evaporated off. 6.9 g of oily product are obtained, and this is dissolved in isopropyl alcohol, a stream of gaseous hydrochloric acid is passed through it and the salt is recrystallized in ethanol. 7.8 g of dihydrochloride are obtained. Melting point: 260°–265° C.

Second variant 60 g (179 mmol) of 2-[(1-phenylmethyl-4-piperidyl)carbonyl]-1,2,3,4-tetrahydroisoquinoline are introduced portionwise under an argon atmosphere into a suspension of 10.2 g (268 mmol) of lithium aluminium hydride in 3 l of ether heated under reflux. Stirring is maintained for 2 h, and the mixture is then cooled in an ice bath and hydrolysed with 24.12 ml of 1N sodium hydroxide. The insoluble material is filtered off, the filtrate concentrated, the residue taken up in ether and a stream of hydrogen chloride gas passed through it. The salt which precipitates is filtered off and dried. 66.7 g of dihydrochloride are obtained. Melting point: 259°–264° C.

EXAMPLE 3

(Compound No. 1)

2-[(4-Piperidyl)methyl]-1,2,3,4-tetrahydroisoquinoline dihydrochloride (a) First variant 5.8 g (23.7 mmol) of 2-[(4-piperidyl)carbonyl]-1,2,3,4-tetrahydroisoquinoline are added under an argon atmosphere to a solution of 0.9 g (23.7 mmol) of lithium aluminium hydride in 150 ml of ether. The mixture is heated under reflux for 7 h. It is cooled, and hydrolysed with 2 ml of water, the insoluble material is filtered off, the organic phase is separated off and dried, the solvent is evaporated off, and the residue is taken up in a mixture of isopropyl alcohol and methanol and a stream of gaseous hydrochloric acid is passed through it. 3.7 g of dihydrochloride are thereby obtained. Melting point: 252°–255° C.

(b) Second variant

A mixture of 11.2 (28.4 mmol) of 2-[(1-phenylmethyl-4-piperidyl)methyl]-1,2,3,4-tetrahydroisoquinoline dihydrochloride, 1.5 g of palladinized charcoal (10% palladium) and 200 ml of ethanol is subjected to a catalytic hydrogenation under a hydrogen pressure of approximately 0.41 MPa and at a temperature of 40° C. The catalyst is filtered off, it being rinsed with ethanol, the filtrate evaporated and the residue recrystallized in ethanol. 6.9 g of dihydrochloride are obtained. Melting point: 252°–255° C.

EXAMPLE 4

(Compound No. 2)

2-[(1-Methyl-4-piperidyl)methyl]-1,2,3,4-tetrahydroisoquinoline difumarate.

(a)

1-Methyl-4-[(1,2,3,4-tetrahydro-2-isoquinolyl)carbonyl]pyridinium iodide 2 ml, equivalent to 4.26 g (30.2 mmol) of iodomethane and 6 g (25.2 mmol) of 2-[(4-pyridyl)carbonyl]-1,2,3,4-tetrahydroisoquinoline are introduced into 200 ml of ethyl acetate, and the mixture is stirred for 24 h at room temperature. A yellow precipitate forms, which is filtered off and washed with ether. 8.3 g of product are obtained, this being used without further treatment in the following stage.

(b)

2-[(1-Methyl-4-piperidyl)carbonyl]-1,2,3,4-tetrahydroisoquinoline 4 g (10.5 mmol) of 1-methyl-4-[(1,2,3,4-tetrahydro-2-isoquinolyl)carbonyl]pyridinium iodide and 0.4 g of platinum oxide are introduced into 250 ml of methanol, and the mixture is subjected to hydrogenation for 12 h under a pressure of approximately 0.41 MPa. The catalyst is filtered off, the solvent evaporated off and the residue neutralized, and an oil is obtained which crystallizes and which is used without further treatment in the following stage.

(c)

2-[(1-Methyl-4-piperidyl)methyl]-1,2,3,4-tetrahydroisoquinoline difumarate 3 g (11.6 mmol) of 2-[(1-methyl-4-piperidyl)carbonyl]-1,2,3,4-tetrahydroisoquinoline are dissolved under an argon atmosphere in 100 ml of tetrahydrofuran, 0.9 g of lithium aluminium hydride is added and the mixture is heated under reflux for 4 h. Stirring is continued for 12 h at room temperature, the mixture is then hydrolysed with sodium hydroxide and the organic phase is separated off and evaporated. A yellow oil is obtained, the difumarate of which is prepared. Melting point: 157°–158° C.

EXAMPLE 5

(Compound No. 14)

2-[(1-Phenylcarbonyl-4-piperidyl)methyl]-1,2,3,4-tetrahydroisoquinoline hydrochloride (a)

2-[(4-Piperidyl)carbonyl]-1,2,3,4-tetrahydroisoquinoline 115 g (0.34 mol) of 2-[(1-phenylmethyl-4-piperidyl)carbonyl]-1,2,3,4-tetrahydroisoquinoline are dissolved in 1 l of acetic acid, 4 g of palladinized charcoal (10% palladium) are added and the mixture is subjected to a hydrogenation at 75° C. under 0.35 MPa.

When the absorption of hydrogen is complete, the mixture is allowed to return to room temperature, the catalyst is filtered off and the filtrate is concentrated under reduced pressure. The residue is taken up with water and cooled in an ice bath, sodium hydroxide is added to it to pH 10 and it is extracted with dichloromethane. The organic phase is washed with water, and dried over sodium sulphate, the solvent evaporated off and the residue crystallized in dry ether. The crystals are filtered off, washed with pentane and dried under vacuum. 73.5 g of product are obtained. Melting point: 201°–205° C. (slow decomposition).

(b)

2-[(4-Piperidyl)methyl]-1,2,3,4-tetrahydroisoquinoline hydrochloride 5.8 g (23.7 mmol) of 2-[(4-piperidyl)carbonyl]-1,2,3,4-tetrahydroisoquinoline are added under an argon atmosphere to a suspension of 0.9 g (23.7 mmol) of lithium aluminium hydride in 150 ml of ether. The mixture is heated under reflux for 7 h. It is cooled, and hydrolysed with 2 ml of water, the insoluble material is filtered off, the organic phase is evaporated off and dried, the solvent is evaporated off, and the residue is taken up in a mixture of isopropyl alcohol and methanol and a stream of gaseous hydrochloric acid is passed through it. 3.7 g of dihydrochloride are thereby obtained. Melting point: 252°–255° C.

(c)

2-[(1-Phenylcarbonyl-4-piperidyl)methyl]-1,2,3,4-tetrahydroisoquinoline hydrochloride 3.9 g (0.024 mol) of N,N'-carbonyldiimidazole are added in small portions to a solution of 2.68 g (0.022 mol) of benzoic acid in 75 ml of tetrahydrofuran, placed under an argon atmosphere. The reactor is immersed in a bath of lukewarm water and the mixture stirred for 1 h.

4.6 g (0.02 mol) of 2-[(4-piperidyl)methyl]-1,2,3,4-tetrahydroisoquinoline dissolved in 75 ml of tetrahydrofuran are then added, and the mixture is stirred for 6 h at room temperature and then for 9 h under reflux.

The mixture is poured into ice-cold water and extracted with dichloromethane, the organic phase separated off, washed with ammonia solution and then with water and dried over magnesium sulphate and the solvent evaporated off under reduced pressure.

6.2 g of oily product are obtained, and this is purified by chromatography on a silica column, eluting with a 98:2 dichloromethane/methanol mixture. The base is dissolved in a little isopropyl alcohol, a stream of gaseous hydrochloric acid is passed through it, and the hydrochloride which precipitates is filtered off and recrystallized three times in ethanol. 3.0 g of hydrochloride are finally isolated. Melting point: 228°–235° C. (decomposition).

EXAMPLE 6

(Compound No. 16)

2-[{1-[(3-Chlorophenyl)carbonyl]-4-piperidyl}methyl]-1,2,3,4-tetrahydroisoquinoline hydrochloride 4.6 g (0.02 mol) of 2-[(4-piperidyl)methyl]-1,2,3,4-tetrahydroisoquinoline, 2 g, equivalent to 2.8 ml (0.02 mol), of trimethylamine and 1 ml of ethyl acetate are introduced into a round-bottomed flask. While the temperature is maintained at approximately 20° C. using a cold bath, 3.5 g, equivalent to 2.6 ml (0.02 mol), of 3-chlorobenzoyl chloride dissolved in 50 ml of ethyl acetate are then added dropwise. The mixture is stirred for 2 h, the precipitate filtered off and washed with ethyl acetate, the filtrate washed with water and dried and the solvent evaporated off.

6.8 g of oily residue are obtained, and this is redissolved in ethyl acetate, ethereal hydrochloric acid is added, the mixture is stirred for 20 min, and the hydrochloride is drained, washed with ether and recrystallized in a 50:50 isopropyl alcohol/ethyl acetate mixture. 6.5 g of white crystals are finally isolated. Melting point: 162°–163° C.

EXAMPLE 7

(Compound No. 19)

2-[{1-[(3-methylphenyl)carbonyl]-4-piperidyl}methyl]-1,2,3,4-tetrahydroisoquinoline fumarate 4.6 g (0.02 mol) of 2-[(4-piperidyl)methyl]-1,2,3,4-tetrahydroisoquinoline are dissolved in 50 ml of dichloromethane, 2.23 g, equivalent to 3.1 ml (0.022 mol) of triethylamine are added, and a solution of 3.4 g (0.022 mol) of 3-methylbenzoyl chloride dissolved in 10 ml of dichloromethane is then added dropwise in the course of 20 min. The temperature of the mixture rises to 38° C. The mixture is stirred at room temperature overnight, then poured into water and extracted with dichloromethane, the organic phase is washed four times with saturated sodium chloride solution and dried over sodium sulphate and the solvent is evaporated off under reduced pressure. 7.8 g of brown oily residue are obtained, and this is purified by chromatography on a silica column, eluting with a 90:10 dichloromethane/methanol mixture, thereby yielding 6.9 g of purified product.

3.45 g of this are dissolved in 50 ml of ethanol and a solution of 1.05 g of fumaric acid in 100 ml of ethanol is added thereto. The mixture is stirred for 30 min, the solvent then evaporated off under reduced pressure, the residue taken up with 250 ml of acetone and the mixture left to crystallize in the cold, and the crystals are filtered off and dried under reduced pressure at 90° C. 2.7 g of fumarate are finally isolated. Melting point: 149°–151° C.

EXAMPLE 8

(Compound No. 27)

2-[{1-[(3-Trifluoromethylphenyl)carbonyl]-4-piperidyl}methyl]-1,2,3,4-tetrahydroisoquinoline fumarate A mixture of 5.2 g (0.026 mol) of 2-[(4-piperidyl)methyl]-1,2,3,4-tetrahydroisoquinoline and 3.8 ml (0.027 mol) of triethylamine dissolved in 20 ml of dichloromethane is added dropwise to a solution of 4.7 g (0.0226 mol) of 3-trifluoromethylbenzoyl chloride in 20 ml of dichloromethane, cooled in an ice bath.

The mixture is stirred for 20 h at room temperature and then filtered, and the filtrate is washed with water, dried and evaporated under reduced pressure. The residual oil is purified by chromatography on a silica column, 7 g of an oil are obtained and this is dissolved in 20 ml of methanol, this solution is added to 2.02 g of fumaric acid dissolved in 20 ml of methanol, the mixture is evaporated, the residue is crystallized in ether and the solid is then recrystallized in isopropyl alcohol. 7.4 g of fumarate are finally isolated. Melting point: 162°–164° C.

EXAMPLE 9

(Compound No. 41)

2-[(1-Phenylcarbonylmethyl-4-piperidyl)methyl]-1,2,3,4-tetrahydroisoquinoline difumarate 3.46 g (15 mmol) of 2-(4-piperidylmethyl)-1,2,3,4-tetrahydroisoquinoline are dissolved in 20 ml of dry dichloromethane, 4.05 g (44 mmol) of dry triethylamine are added, and a solution of 3 g (15 mmol) of 2-bromo-1-phenyl-1-ethanone dissolved in 80 ml of dichloromethane are then added dropwise to this mixture. The suspension is stirred for 3 h at room temperature and then concentrated under reduced pressure. The evaporation residue is washed with water, the oil extracted with dichloromethane and the organic phase is separated off, dried over magnesium sulphate and concentrated under reduced pressure. The residue is purified by chromatography on a silica column, eluting with a 95:5 dichloromethane/methanol mixture. A red oil is recovered, which is dissolved in ether. An insoluble material forms which is removed by filtration, and the filtrate is concentrated. The difumarate is prepared by dissolving 2.1 g of fumaric acid in 50 ml of methanol and adding 3.34 g of base dissolved in 30 ml of ethyl acetate thereto. The salt crystallizes, and it is washed with ethyl acetate and then with ether and dried under vacuum. Melting point: 203°–205° C.

EXAMPLE 10

(Compound No. 45)

2-[{1-[(4-Fluorophenyl)methyl]-4-piperidyl}methyl]-1,2,3,4-tetrahydroisoquinoline difumarate 3.6 g (10 mmol) of 2-[{1-[(4-fluorophenyl)carbonyl]-4-piperidyl}methyl]-1,2,3,4-tetrahydroisoquinoline are dissolved under an argon atmosphere in 40 ml of tetrahydrofuran, and 40 ml (40 mmol) of a molar solution of borane/tetrahydrofuran complex in tetrahydrofuran are added dropwise in the course of 10 min.

The mixture is stirred for 15 min, heated under reflux for 4 h and then left to stand at room temperature. The complex is destroyed by adding 10 ml of methanol followed by 5 ml of concentrated hydrochloric acid, and the mixture is heated for a further 6 h under reflux.

The solvents are evaporated off under reduced pressure, the residue is taken up with water and its pH is adjusted to 10 by means of concentrated ammonia solution.

The mixture is extracted by means of ethyl acetate, and the organic phase washed with saturated sodium chloride solution to neutrality and dried over sodium sulphate.

The solvent is evaporated off under reduced pressure, and 4.2 g of an orange oil which partially crystallizes are obtained. It is dissolved in 100 ml of ethanol, the solution is filtered and a solution of 1.85 g (16 mmol) of fumaric acid in 100 ml of ethanol is added to the filtrate.

A yellow solution is obtained, which partially crystallizes. It is evaporated under reduced pressure and the residue is recrystallized in 150 ml of ethanol, washed with ice-cold ether and dried under vacuum. 3.4 g of difumarate are isolated. Melting point: 183°–185° C.

EXAMPLE 11

(Compound No. 49)

2-[{1-[(3,4-Dimethoxyphenyl)methyl]-4-piperidyl}methyl]-1,2,3,4-tetrahydroisoquinoline difumarate (a)

1-[(3,4-Dimethoxyphenyl)methyl]-4-[(1,2,3,4-tetrahydro-2-isoquinolyl)carbonyl]pyridinium chloride A mixture of 4.76 g (20 mmol) of 2-[(4-pyridyl)carbonyl]-1,2,3,4-tetrahydroisoquinoline, 4.5 g (24 mmol) of 3,4-dimethoxybenzyl chloride and 200 ml of ethyl acetate is heated under reflux for 20 h. The mixture obtained is allowed to cool, and the precipitate is separated off by filtration and washed with ether. 6.6 g of salt are collected, this being used without further purification in the following stage.

(b)

2-[{1-[(3,4-Dimethoxyphenyl)methyl]-4-piperidyl}carbonyl]-1,2,3,4-tetrahydroisoquinoline 6.5 g of 1-[(3,4-dimethoxyphenyl)methyl]-4-[(1,2,3,4-tetrahydro-2-isoquinolyl)carbonyl]pyridinium chloride, 300 ml of ethanol and 0.7 g of platinum oxide are introduced into a Parr bottle.

The mixture is stirred under a hydrogen pressure 0.35 MPa until the absorption is complete, equivalent to approximately 18 h. The catalyst is filtered off and washed with ethanol, and the filtrate is evaporated, neutralized with ammonia solution and extracted with dichloromethane.

The organic phase is washed with water and dried, and the solvent evaporated off. 6 g of an oil are collected, this being used without further purification in the following stage.

(c)

2-[{1-[(3,4-Dimethoxyphenyl)methyl]-4-piperidyl}methyl]-1,2,3,4-tetrahydroisoquinoline A suspension of 0.6 g (15.8 mmol) of lithium aluminium hydride in 50 ml of tetrahydrofuran is stirred for 10 min, and 3 g (7.6 mmol) of 2-[{1-(3,4-dimethoxyphenyl)methyl]-4-piperidyl}-carbonyl]-1,2,3,4-tetrahydroisoquinoline dissolved in 100 ml of tetrahydrofuran are then added slowly.

The mixture is heated under reflux for 5 h and allowed to cool, 1N sodium hydroxide is added, the mixture is stirred for 20 min, the inorganic precipitate is filtered off, it being washed with ether, and the filtrate is washed with water, dried and evaporated. 2.2 g of a yellow oil are collected, the fumarate of which is prepared by treating it with two equivalents of fumaric acid, and the difumarate is recrystallized in ethanol. Melting point: 175°–176° C.

EXAMPLE 12

(Compound No. 51)

2-[{1-[(3-Cyanophenyl)methyl]-4-piperidyl}methyl]-1,2,3,4-tetrahydroisoquinoline difumarate A mixture of 6.79 g (31 mmol) of 2-[(4-piperidyl)methyl]-1,2,3,4-tetrahydroisoquinoline, 7.29 g (37 mmol) of 3-(bromomethyl)benzenenitrile, 10.7 g (77 mmol) of potassium carbonate and 70 ml of acetone is stirred for 15 h. The mixture is filtered, the filtrate is evaporated, water and dichloromethane are added, and the organic phase is separated off, washed with water, dried over magnesium sulphate and evaporated. The residue is purified by chromatography on a silica column, eluting first with a 97:3 dichloromethane/methanol mixture, and then a 96:4 dichloromethane/methanol mixture. 6.2 g of a yellow oil are obtained.

3 g (8.6 mmol) of this are dissolved in ethyl acetate, and this solution is poured into a solution of 1.99 g (17.2 mmol) of fumaric acid dissolved in the minimum amount of ethanol. 4.1 g of difumarate are finally collected. Melting point: 179°–181° C.

EXAMPLE 13

(Compound No. 52)

2-[{1-[(3-Aminocarbonylphenyl)methyl]-4-piperidyl}methyl]-1,2,3,4-tetrahydroisoquinoline difumarate A stream of gaseous hydrochloric acid is bubbled through a mixture of 2.3 g (66 mmol) of 2-[{1-[(3-cyanophenyl)methyl]-4-piperidyl}methyl]-1,2,3,4-tetrahydroisoquinoline (free base) and 30 ml of formic acid, the disappearance of the starting compound being followed by thin layer chromatography.

When the reaction is complete, water, ammonia solution and dichloromethane are added, and the organic phase is separated off, washed with water, dried over magnesium sulphate, filtered and evaporated. 3.18 g of a yellow oil are obtained, and this is purified by chromatography on a silica column, eluting with dichloromethane/methanol mixtures in successive proportions of 95:5, 94:6, 93:7, 92:8, 91:9 and 90:10. 1.5 g (4.1 mmol of pure base are thereby isolated, and this is dissolved in ethyl acetate and poured dropwise into 0.85 g (8.2 mmol) of fumaric acid dissolved in the minimum amount of methanol. The mixture obtained is evaporated and washed with ether and then with ethyl acetate. 1.5 g of difumarate are finally isolated. Melting point: 182°–184° C.

EXAMPLE 14

(Compound No. 53)

2-[{1-[(3-Nitrophenyl)methyl]-4-piperidyl}methyl]-1,2,3,4-tetrahydroisoquinoline difumarate (a)

2-[{1-[(3-Nitrophenyl)methyl]-4-piperidyl}carbonyl]-1,2,3,4-tetrahydroisoquinoline A mixture of 7 g (28.6 mmol) of 2-[(4-piperidyl)carbonyl]-1,2,3,4-tetrahydroisoquinoline, 6.8 g (31.5 mmol) of α-bromo-3-nitrotoluene and 6 g (43 mmol) of potassium carbonate in 140 ml of acetone is stirred for 15 h. The solvent is evaporated off, water and dichloromethane are added and the organic phase is separated off, neutralized, dried and evaporated. 13 g of a yellow oil are obtained, and this is purified by chromatography on a silica column, eluting with a 98:2 dichloromethane/methanol mixture. After recrystallization in ether, 9.6 g of product are obtained, this being used without further purification in the following stage.

(b)

2-[{1-[(3-Nitrophenyl)methyl]-4-piperidyl}methyl]-1,2,3,4-tetrahydroisoquinoline difumarate A mixture of 6.6 g (17.4 mmol) of 2-[{1-[(3-nitrophenyl)methyl]-4-piperidyl}carbonyl]-1,2,3,4-tetrahydroisoquinoline and 1.44 g (52 mmol) of diborane in 90 ml of tetrahydrofuran is heated under reflux for 5 h. The mixture is left to stand and then hydrolysed by adding 20 ml of methanol and 5 ml of concentrated hydrochloric acid. It is heated under reflux for 3 h, evaporated and taken up with water, activated charcoal is added, the mixture is stirred for 1 h at room temperature and filtered and the filtrate is neutralized. The organic phase is separated off and dried, the solvent evaporated off under reduced pressure and the residue purified by chromatography on a silica column, eluting with a 97:3 dichloromethane/methanol mixture.

After recrystallization in pentane, 5.27 g of purified base are obtained. The difumarate is prepared by treating 2.5 g (6.84 mmol) of base with 1.59 g (13.7 mmol) of fumaric acid, in methanol. Melting point: 216°–217° C.

EXAMPLE 15

(Compound No. 54)

2-[{1-[(3-Aminophenyl)methyl]-4-piperidyl}methyl]-1,2,3,4-tetrahydroisoquinoline difumarate A solution of 2.7 g (7.4 mmol) of 2-[{1-[(3-nitrophenyl)methyl]-4-piperidyl}methyl]-1,2,3,4-tetrahydroisoquinoline in 135 ml of acetic acid is subjected to a catalytic hydrogenation under a pressure of 0.35 MPa, in the presence of palladinized charcoal, until the absorption of hydrogen is complete.

The catalyst is filtered off, the filtrate concentrated under reduced pressure and the residue purified by chromatography on a silica column, eluting with a 90:10 dichloromethane/methanol mixture. After recrystallization in pentane, 1.9 g of purified base are collected.

0.242 g (2.08 mmol) of fumaric acid and 0.349 g (1.04 mmol) of base are dissolved in the minimum amount of ethanol, the two solutions are combined, the solvent is evaporated off and the residue is recrystallized in isopropyl alcohol. 0.460 g of difumarate are finally isolated. Melting point: 163°–166° C.

EXAMPLE 16

(Compound No. 55)

2-[{1-[(3-Dimethylaminophenyl)methyl]-4-piperidyl}methyl]-1,2,3,4-tetrahydroisoquinoline difumarate 0.805 g (26.8 mmol) of formaldehyde is dissolved in 30 ml of tetrahydrofuran, and 1.1 g (11.2 mmol) of concentrated sulphuric acid are added, followed by 1.5 g (4.47 mmol) of 2-[{1-[(3-aminophenyl)methyl]-4-piperidyl}methyl]-1,2,3,4-tetrahydroisoquinoline. The mixture is stirred for 30 min at room temperature and then cooled in an ice bath, and 1.184 g (31.3 mmol) of sodium borohydride are gradually added thereto without the pH rising above 4.

Stirring is maintained at room temperature for 3 h, the mixture is then evaporated, carbonated water and dichloromethane are added to the residue, the organic phase is separated off, filtered and dried, the solvent is evaporated off under reduced pressure and the residue is purified by chromatography on a silica column. 0.400 g of purified base is obtained.

0.364 g (1 mmol) of this is used for preparing with difumarate with 0.221 g (1.9 mmol) of fumaric acid, according to the procedure described in the preceding example. 0.250 g of difumarate is finally collected. Melting point: 180°–182° C.

EXAMPLE 17

(Compound No. 61)

2-[{1-[(2-Pyridyl)carbonyl]-4-piperidyl}methyl]-1,2,3,4-tetrahydroisoquinoline fumarate 10.05 ml (24 mmol) of trimethylaluminium (at a concentration of 25% in hexane) are added under an argon atmosphere to 20 ml of toluene. The mixture is cooled in an ice bath and 4.6 g (20 mmol) of 2-[(4-piperidyl)methyl]-1,2,3,4-tetrahydroisoquinoline, diluted in 25 ml of toluene, are added.

The mixture is heated to approximately 50° C. and 3.02 g (20 mmol) of ethyl 2-pyridinecarboxylate, dissolved in 15 ml of toluene, are added, approximately 10 ml of solvents is removed by means of a Dean and Stark apparatus and the mixture is heated under reflux for 3 h.

It is then cooled in an ice bath, hydrolysed with 10 ml of water and filtered, the solid being rinsed with ethyl acetate, the filtrate is washed three times with water, dried over magnesium sulphate and filtered and the solvent is evaporated off under reduced pressure.

6.7 g (20 mmol) of free base are obtained, and this is dissolved in the minimum amount of ethanol, and a solution of 2.3 g (20 mmol) of fumaric acid in 300 ml of ethanol is added. The ethanol is evaporated off and the residue recrystallized in ethanol. 5 g of fumarate are finally isolated. Melting point: 115°–118° C.

EXAMPLE 18

(Compound No. 68)

2-[{1-[(2-Indolyl)carbonyl]-4-piperidyl}methyl]-1,2,3,4-tetrahydroisoquinoline fumarate 4.05 g (25 mmol) of N,N-carbonyldiimidazole is added in small portions under an argon atmosphere to a solution of 3.7 g (23 mmol) of 2-indolecarboxylic acid in 37 ml of tetrahydrofuran.

The mixture is stirred for 3 h at room temperature and the solvent then evaporated off. The residue is taken up with 46 ml of dichloromethane and this solution is added to a solution of 4.6 g (20 mmol) of 2-[(4-piperidyl)methyl]-1,2,3,4-tetrahydroisoquinoline in 40 ml of dichloromethane.

The mixture is stirred for 12 h and then poured into water. It is extracted with dichloromethane, the organic phase washed four times with water, dried over magnesium sulphate and filtered, the solvent evaporated off under reduced pressure and the residue recrystallized in tetrahydrofuran.

5 g (13.3 mmol) of free base are obtained; this is introduced into a mixture of dichloromethane and methanol and a solution of 1.55 g (13.3 mmol) of fumaric acid in 200 ml of ethanol is added. The mixture is heated under reflux, ethanol is added until dissolution is complete, the solvents are then evaporated off under reduced pressure and the residue is recrystallized in ethanol. 5.5 g of fumarate are finally isolated. Melting point: 203°–206° C.

EXAMPLE 19

(Compound No. 65)

2-[{1-[(3-Thienyl)carbonyl]-4-piperidyl}methyl]-1,2,3,4-tetrahydroisoquinoline fumarate (a) 3-Thiophenecarboxylic acid chloride 5.12 g (44 mmol) of 3-thiophenecarboxylic acid are added to 50 ml of thionyl chloride, the mixture is heated to boiling for 2 h and then evaporated, the residue is taken up with toluene and the latter is evaporated off. 5 g of residue are obtained, this being used without further treatment in the following stage.

(b) 2-[{1-[(3-thienyl)carbonyl]-4-piperidyl}methyl]-1,2,3,4-tetrahydroisoquinoline 2.5 g (17 mmol) of 3-thiophenecarboxylic acid chloride dissolved in 20 ml of dichloromethane are added at room temperature to a solution of 4.6 g (20 mmol) of 2-[(4-piperidyl)methyl]-1,2,3,4-tetrahydroisoquinoline and 3.06 ml (22 mmol) of triethylamine in 46 ml of dichloromethane, and the mixture is stirred for 48 h. Since the reaction is not complete, a further 2.5 g (17 mmol) of acid chloride and 3 ml (22 mmol) of triethylamine dissolved in 20 ml of dichloromethane are added.

The mixture is stirred for a further 1 h, poured into water and extracted with dichloromethane; the organic phase is washed twice with water, dried over magnesium sulphate and filtered, and the solvent is evaporated off under reduced pressure.

The residue is purified by chromatography on a silica column, eluting with a 98:2 dichloromethane/methanol mixture. 3 g (8.8 mmol) of base are obtained, this is dissolved in a mixture of dichloromethane and ethanol and a solution of 1 g (8.8 mmol) of fumaric acid in 100 ml of ethanol is added. The solvents are evaporated off and the residue is recrystallized in ethanol. 3.3 g of fumarate are finally isolated. Melting point: 174°–177° C.

EXAMPLE 20

(Compound No. 74)

2-{[-1-(Trifluoroacetyl)-4-piperidyl]methyl}-1,2,3,4-tetrahydroisoquinoline hydrochloride 2.3 g (11 mmol) of trifluoroacetic anhydride dissolved in 50 ml of tetrahydrofuran are added dropwise to a mixture of 2.3 g (10 mmol) of 2-[(4-piperidyl)methyl]-1,2,3,4-tetrahydroisoquinoline, 1.4 ml (10 mmol)

of triethylamine and 100 ml of tetrahydrofuran, cooled to 0° C. The temperature is allowed to return to 20° C. and stirring is maintained for 20 h.

The mixture is filtered, the filtrate washed with 10% strength aqueous sodium hydroxide solution and then with water, dried over magnesium sulphate and filtered, and the solvent evaporated off under reduced pressure.

1.7 g of oily residue, which crystallizes, are obtained. The hydrochloride of this is prepared by adding 0.1N hydrochloric acid in isopropyl alcohol, and is recrystallized in ethanol. Melting point: 195°–196° C.

EXAMPLE 21

(Compound No. 19)

2-[{1-[(3-Methylphenyl)carbonyl]-4-piperidyl}methyl]-1,2,3,4-tetrahydroisoquinoline fumarate (a) 4-Piperidinemethanol 28.5 g (0.75 mol) of lithium aluminium hydride and 1.2 l of tetrahydrofuran are introduced into a 4-l three-necked round-bottomed flask equipped with a mechanical stirring system and a condenser. 117.9 g (0.75 mol) of ethyl 4-piperidinecarboxylate dissolved in 1.2 l of tetrahydrofuran are added to the suspension obtained, and the mixture is stirred for 6 h at 20° C. It is cooled to 0° C., and then hydrolysed by adding successively 22 ml of water, 22 ml of 1N sodium hydroxide and 46 ml of water. The mixture is stirred for 30 min. at 20° C. and filtered, and the precipitate is washed with tetrahydrofuran and then with ether. The solvents are evaporated off under reduced pressure and 84.4 g of an oil are obtained, this being used without further treatment in the following stage.

(b) [1-(3-Methylbenzoyl)-4-piperidyl]methyl 3-methylbenzoate 42.25 g (0.367 mol) of 4-piperidinemethanol and 430 ml of 1,2-dichloroethane are introduced under an argon atmosphere into a 3-l three-necked round-bottomed flask, and 82 g (0.81 mol) of triethylamine are added, followed by 125.2 g (0.81 mol) of 3-methylbenzoyl chloride. The mixture is heated under reflux for 4 h 30 min., a further 8.2 g (0.08 mol) of triethylamine and 12.5 g (0.08 mol) of 3-methylbenzoyl chloride are added, and the mixture is heated for a further 3 h.

It is filtered, the salts are washed with 1,2-dichloroethane, the filtrate is evaporated under reduced pressure, the residue is dissolved in ethyl acetate, the solution is washed with saturated aqueous sodium chloride solution, the solvent is evaporated off under reduced pressure and the residue is recrystallized in a 1:1 isopropyl alcohol/ethyl acetate mixture. 80 g of white solid are obtained. Melting point: 80°–83° C.

(c) 1-(3-Methylbenzoyl)-4-piperidinemethanol

A solution of 12.76 g (0.23 mol) of potassium hydroxide in 75 ml of ethanol and 75 ml of water is added to a solution of 80 g (0.23 mol) of [1-(3-methylbenzoyl)-4-piperidyl]methyl 3-methylbenzoate in 400 ml of ethanol. The mixture is stirred at 20° C. for 3 h, the solvent evaporated off under reduced pressure and the aqueous phase extracted with ethyl acetate. The organic phase is washed with water and then with saturated aqueous sodium chloride solution, and dried over magnesium sulphate. The solvent is evaporated off under reduced pressure and 53 g of alcohol are obtained, this being used without further treatment in the following stage.

(d) [1-(3-Methylbenzoyl)-4-piperidyl]methyl 4-methylbenzenesulphonate 53.3 g (0.28 mol) of 4-methylbenzenesulphonyl chloride in 60 ml of pyridine are added to a solution of 52 g (0.22 mol) of 1-(3-methylbenzoyl)-4-piperidinemethanol in 100 ml of pyridine. The mixture is stirred at 20° C. for 4 h, and then poured into ice. The phase is extracted with dichloromethane, and the organic phase washed with 10N aqueous hydrochloric acid solution and dried over magnesium sulphate. The solvents are evaporated off under reduced pressure and 70 g of white solid are obtained.

Melting point: 68°–70° C.

(e) 2-[{1-(3-methylphenyl)carbonyl]-4-piperidyl}methyl]-1,2,3,4-tetrahydroisoquinoline fumarate A mixture of 2.66 g (0.02 mol) of 1,2,3,4-tetrahydroisoquinoline and 7.75 g (0.02 mol) of [1-(3-methylbenzoyl)-4-piperidyl]methyl 4-methylbenzenesulphonate is heated for 4 h to 150° C. The mixture is allowed to cool and is dissolved in dichloromethane, and concentrated ammonia solution is added. The organic phase is separated off, washed three times with water, dried over magnesium sulphate and evaporated under reduced pressure, and the residual oil is purified by chromatography on a silica column, eluting with a 98:2 dichloromethane/methanol mixture. 2 g (0.0057 mol) of pure base are obtained, this is dissolved in ethanol, 0.66 g (0.0057 mol) of fumaric acid dissolved in 100 ml of ethanol is added, the ethanol is evaporated off and the residue is recrystallized in acetone. 2 g of fumarate are finally isolated. Melting point: 149°–151° C.

EXAMPLE 22

(Compound No. 8)

2-[{1-[(3-Methylphenyl)methyl]-4-piperidyl}methyl]-1,2,3,4-tetrahydroisoquinoline difumarate 1.36 g of 2-[{1-[(3-methylphenyl)carbonyl]-4-piperidyl}methyl]-1,2,3,4-tetrahydroisoquinoline are dissolved in 30 ml of dry ether, 0.29 g of lithium aluminium hydride is added in a single portion and the mixture is stirred at room temperature for 3 h. It is cooled in an ice bath, hydrolysed with 2.4 ml of 1N sodium hydroxide and filtered, and the filtrate is evaporated. 1.2 g (0.0035 mol) of base are obtained, this is dissolved in the minimum amount of ethanol, 0.82 g (0.0035 mol) of fumaric acid dissolved in 100 ml of ethanol is added, and the precipitate is filtered off and dried. 1.2 g of difumarate are finally obtained. Melting point: 185°–186° C.

The compounds of the invention were subjected to a series of pharmacological tests which demonstrated their value as substances having therapeutic activity.

Thus, they were subjected to a study in respect of their affinity for 5-HT$_{1A}$ type serotoninergic receptors present in the rat hippocampus.

The compounds displace the binding of a labelled specific ligand, [$^3$H]-8-hydroxy-2-di-n-propylaminotetralin (hereinafter designated "[$^3$H]-8-OH-DPAT" and described by Gozlan et al., Nature, (1983), 305, 140–142), to the 5-HT$_{1A}$ receptors.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion for 10 min at 48,000×g and resuspending the pellet in cooled fresh buffer. Finally, the last pellet is suspended in the buffer to produce a concentration of 100 mg of original tissue per ml of 50 mM buffer. The suspension is then left to incubate at 37° C. for 10 min.

The binding with [$^3$H]-8-OH-DPAT is determined by incubating 100 μl of membrane suspension in a final volume of 1 ml of buffer containing 10 μM pargyline and 3 μM paroxetine.

After an incubation for 15 min at 37° C. the membranes are recovered by filtration on Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OH-DPAT is defined as the quantity of radioactivity retained on the filters and capable of being inhibited by coincubation in 10 μM 5-hydroxytryptamine. At a [$^3$H]-8-OH-DPAT concentration of 1 nM, the specific binding represents 90% of the total radioactivity recovered on the filter.

For each concentration of test compound, the percentage inhibition of the binding with [$^3$H]-8-OH-DPAT, and then the IC$_{50}$ concentration, the concentration which inhibits 50% of the binding, are determined.

For the compounds of the invention, the IC$_{50}$ value lies between 0.001 and 0.3 μM.

The central activity of the compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358–361 (Karger, Basel 1977).

Cumulative doses of test compounds are administered (from 0.001 to 3 mg/kg intravenously) at 30-min. time intervals, 4 h after the intraperitoneal injection of a dose of 0.75 mg/kg of reserpine, to curarized cats under artificial ventilation. The electroencephalographic and phasic (PGO-R spike) activities are obtained using cortical and deep (lateral geniculate) electrodes. For each dose of test compound, the percentage decrease in the number of PGO spikes, and then the AD$_{50}$, the active dose which decreases this number of spikes by 50%, are determined.

For the compounds of the invention, the intravenous ED$_{50}$ values lie between 0.001 and 1 mg/kg.

The results of the tests show that the compounds of formula (I) possess, in vitro, a high affinity and a selectivity for 5-HT$_{1A}$ type serotoninergic receptors. In vivo, they show an agonist, partial agonist or antagonist activity with respect to these receptors.

The compounds of the invention may hence be used for the treatment of diseases and conditions directly or indirectly involving the 5-HT$_{1A}$ type serotoninergic receptors, in particular for the treatment of depressive states, anxiety states and sleep disorders, and for the regulation of food intake, and also for the treatment of vascular, cerebrovascular or cardiovascular conditions such as migraine and hypertension.

Accordingly the present invention provides a compound of formula (I), or a pharmacologically acceptable acid addition salt thereof, for use in a method of treatment of the human or animal body by therapy, especially for use in a method of treatment of a depressive state, an anxiety state, a sleep disorder, or a vascular, cerebrovascular or cardiovascular condition or for use in the regulation of food intake. The present invention additionally provides the use of a compound of formula (I), or a pharmacologically acceptable acid addition salt thereof, in the manufacture of a medicament for the treatment of a depressive state, an anxiety state, a sleep disorder, or a vascular, cerebrovascular or cardiovascular condition or for use in the regulation of food intake.

We claim:

1. A method of treatment of a depressive state which comprises administering, to a subject suffering or liable to suffer from said state an effective amount of the compound of formula (I)

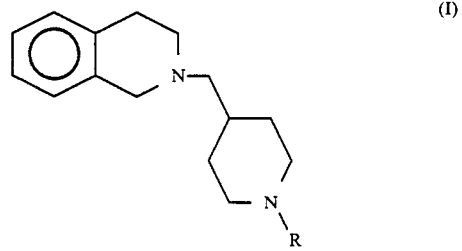

in which R is (a) a hydrogen atom;

(b) a linear or branched (C$_1$–C$_6$) alkyl group; an allyl group; a cycloalkylmethyl group in which the cycloalkyl moiety has from 3 to 6 carbon atoms; a phenylmethyl group unsubstituted or substituted with one to three substituents chosen from halogen atoms and trifluoromethyl, nitro, amino, dimethylamino, cyano, aminocarbonyl, linear or branched (C$_1$–C$_3$) alkyl, linear or branched (C$_1$–C$_3$) alkoxy an linear or branched (C$_1$–C$_3$) alkylthio groups; a 2-phenylethyl group; a 3-phenylpropyl group; a 3-phenyl-2-propenyl group; a phenylcarbonylmethyl group; a naphthylmethyl group; a pyridylmethyl group; a furylmethyl group; or a thienylmethyl group; or (c) a linear or branched (C$_2$–C$_6$) alkanoyl group; a cycloalkylcarbonyl group in which the cycloalkyl moiety has from 3 to 6 carbon atoms; a trifluoroacetyl group; a phenylcarbonyl group unsubstituted or substituted with one to three substituents chosen from halogen atoms and trifluoromethyl, nitro, linear or branched (C$_1$–C$_3$) alkyl, linear or branched (C$_1$–C$_3$) alkoxy and linear or branched (C$_1$–C$_3$) alkylthio groups; a 1-oxo-3-phenyl-2-propenyl group; a naphthylcarbonyl group; a pyridylcarbonyl group; a furylcarbonyl group; a thienylcarbonyl group; a (2-indolyl)carbonyl group; or a (5-indolyl)carbonyl group; or a pharmacologically acceptable acid addition salt thereof.

* * * * *